(12) United States Patent
Tanaka et al.

(10) Patent No.: US 9,475,778 B2
(45) Date of Patent: Oct. 25, 2016

(54) SULFATE OF 5-HYDROXY-1H-IMIDAZOLE-4-CARBOXAMIDE

(71) Applicant: FUJIFILM Corporation, Tokyo (JP)

(72) Inventors: Tomoyuki Tanaka, Toyama (JP); Yu Koseki, Toyama (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/729,130

(22) Filed: Jun. 3, 2015

(65) Prior Publication Data

US 2015/0266826 A1    Sep. 24, 2015

Related U.S. Application Data

(63) Continuation of application No. PCT/JP2014/050590, filed on Jan. 15, 2014.

(30) Foreign Application Priority Data

Jan. 15, 2013  (JP) .................................. 2013-004994

(51) Int. Cl.
  *C07D 233/90*    (2006.01)

(52) U.S. Cl.
  CPC .................................. *C07D 233/90* (2013.01)

(58) Field of Classification Search
  None
  See application file for complete search history.

(56) References Cited

U.S. PATENT DOCUMENTS

| | | |
|---|---|---|
| 4,181,731 A | 1/1980 | Yoshida et al. |
| 4,582,845 A | 4/1986 | Yamahira et al. |
| 8,664,405 B2 | 3/2014 | Kato et al. |
| 2010/0210855 A1 | 8/2010 | Nobuo et al. |

FOREIGN PATENT DOCUMENTS

| | | |
|---|---|---|
| EP | 0 051 962 A2 | 5/1982 |
| EP | 0 159 777 A1 | 10/1985 |
| EP | 2 196 460 A1 | 6/2010 |
| EP | 2 762 469 A1 | 8/2014 |
| JP | 53-32124 A | 3/1978 |
| JP | 57-80328 A | 5/1982 |
| JP | 58-24569 A | 2/1983 |
| JP | 60-185727 A | 9/1985 |
| WO | 2004/083186 A1 | 9/2004 |
| WO | 2009/035168 A1 | 3/2009 |
| WO | 2013/047758 A1 | 4/2013 |

OTHER PUBLICATIONS

International Preliminary Report on Patentability mailed Jul. 30, 2015, for PCT/JP2014/050590.
Stephen M. Berge et al., "Review Article: Pharmaceutical Salts", Journal of Pharmaceutical Sciences, vol. 66, No. 1, Jan. 1977, pp. 1-19, XP000562636.
Extended European Search Report (EESR) dated Oct. 13, 2015 from the European Patent Office in counterpart European Application No. 14740967.6.
Office Action dated Feb. 3, 2016, issued by the State Intellectual Property Office of the P.R.C. in corresponding Chinese Application No. 201480004242.6.
Kazuhide Ashizawa, "Iyakuhin Kessho no Bunshi Jotai ni Kansuru Bussei Hyoka (12) Shio Kesshokei no Saitekika to Kesshoka Gijutsu", Pharm Tech Japan, 2002, pp. 81-96, vol. 18, No. 10.
International Search Report of PCT/JP2014/050590 dated Apr. 8, 2014 [PCT/ISA/210].
Written Opinion of PCT/JP2014/050590 dated Apr. 8, 2014 [PCT/ISA/237].

*Primary Examiner* — Samantha Shterengarts
(74) *Attorney, Agent, or Firm* — Sughrue Mion, PLLC (57) ABSTRACT

Sulfate of 5-hydroxy-1H-imidazole-4-carboxamide has such characteristics as suppressed blue coloring, high purity, low hygroscopic property, and superior storage stability, and thus is useful as an active pharmaceutical ingredient of drugs.

12 Claims, 5 Drawing Sheets

SULFATE OF 5-HYDROXY-1H-IMIDAZOLE-4-CARBOXAMIDE

CROSS REFERENCE OF THE RELATED APPLICATIONS

This application is a Continuation of PCT International Application No. PCT/JP2014/050590 filed on Jan. 15, 2014, which claims priority under 35 U.S.C. 119(a) to Japanese Patent Application No. 2013-004994 filed on Jan. 15, 2013. Each of the above applications is hereby expressly incorporated by reference, in its entirety, into the present application.

TECHNICAL FIELD

The present invention relates to sulfate of 5-hydroxy-1H-imidazole-4-carboxamide.

BACKGROUND ART

5-Hydroxy-1H-imidazole-4-carboxamide (henceforth also referred to as "Compound A") is a compound useful as an anticancer agent (Patent document 1). For the purpose of providing stable Compound A, it has been proposed to make Compound A into an organic sulfonic acid salt (Patent document 2).

PRIOR ART REFERENCES

Patent Documents

Patent document 1: Japanese Patent Unexamined Publication (Kokai) No. 53-32124
Patent document 2: International Publication WO2009/035168

SUMMARY OF THE INVENTION

Object to be Achieved by the Invention

Since, for example, Compound A is easily oxidized, and it easily colors in blue, it cannot be said that Compound A shows satisfactory storage stability. However, it is very important that active pharmaceutical ingredients are highly pure, and stable at room temperature or further higher temperature so as to maintain quality thereof, and show low hygroscopic property.

An object of the present invention is to provide a salt of Compound A showing suppressed coloring in blue, high purity, low hygroscopic property, and superior storage stability.

Means for Achieving the Object

Under such circumstances, the inventors of the present invention conducted various researches, and as a result, found that sulfate (sulfuric acid salt) of Compound A shows suppressed coloring in blue, low hygroscopic property, and superior storage stability, and can be obtained at high purity. They accomplished the present invention on the basis of this finding. Specific means for achieving the object described above are as follows.

[1] Sulfate of Compound A.
[2] A crystal of sulfate of Compound A, which shows diffraction peaks at diffraction angles 2θ of 5.0, 20.3, and 29.6° in a powder X-ray diffraction pattern.

A crystal of sulfate of Compound A, which shows diffraction peaks at diffraction angles 2θ of 5.0, 10.1, 13.6, 14.3, 14.7, 20.3, and 29.6° in a powder X-ray diffraction pattern.
[3] A crystal of sulfate of Compound A, which shows diffraction peaks at diffraction angles 2θ of 5.0, 10.1, 13.6, 14.3, 14.7, 20.3, 27.4, 28.0, 28.8, and 29.6° in a powder X-ray diffraction pattern (henceforth also referred to as "β-form crystal").

The β-form crystal can be distinguished from other crystal forms on the basis of the aforementioned diffraction peaks at the diffraction angles 2θ of 5.0, 20.3, and 29.6°, or the diffraction peaks at the diffraction angles 2θ of 5.0, 10.1, 13.6, 14.3, 14.7, 20.3, and 29.6°. These values are characteristic values of this crystal form.
[4] A pharmaceutical composition containing a crystal of sulfate of Compound A that shows diffraction peaks at diffraction angles 2θ of 5.0, 20.3, and 29.6° in a powder X-ray diffraction pattern; a crystal of sulfate of Compound A that shows diffraction peaks at diffraction angles 2θ of 5.0, 10.1, 13.6, 14.3, 14.7, 20.3, and 29.6° in a powder X-ray diffraction pattern; or a crystal of sulfate of Compound A that shows diffraction peaks at diffraction angles 2θ of 5.0, 10.1, 13.6, 14.3, 14.7, 20.3, 27.4, 28.0, 28.8, and 29.6° in a powder X-ray diffraction pattern.
[5] A crystal of sulfate of Compound A, which shows diffraction peaks at diffraction angles 2θ of 13.7, 17.0, 18.0, and 20.1° in a powder X-ray diffraction pattern.

A crystal of sulfate of Compound A, which shows diffraction peaks at diffraction angles 2θ of 10.0, 13.7, 14.6, 17.0, 18.0, 20.1, 24.4, and 25.2° in a powder X-ray diffraction pattern.
[6] A crystal of sulfate of Compound A, which shows diffraction peaks at diffraction angles 2θ of 10.0, 13.7, 14.6, 17.0, 18.0, 20.1, 24.4, 25.2, and 28.1° in a powder X-ray diffraction pattern (henceforth also referred to as "α-form crystal").

The α-form crystal can be distinguished from other crystal forms on the basis of the aforementioned diffraction peaks at the diffraction angles 2θ of 13.7, 17.0, 18.0, and 20.1°, or the diffraction peaks at the diffraction angles 2θ of 10.0, 13.7, 14.6, 17.0, 18.0, 20.1, 24.4, and 25.2°. These values are characteristic values of this crystal form.
[7] A pharmaceutical composition containing a crystal of sulfate of Compound A that shows diffraction peaks at diffraction angles 2θ of 13.7, 17.0, 18.0, and 20.1° in a powder X-ray diffraction pattern; a crystal of sulfate of Compound A that shows diffraction peaks at diffraction angles 2θ of 10.0, 13.7, 14.6, 17.0, 18.0, 20.1, 24.4, and 25.2°; or a crystal of sulfate of Compound A that shows diffraction peaks at diffraction angles 2θ of 10.0, 13.7, 14.6, 17.0, 18.0, 20.1, 24.4, 25.2, and 28.1°.
[8] A crystal of sulfate of Compound A, which shows diffraction peaks at diffraction angles 2θ of 10.3, 20.7, 20.9, and 31.2° in a powder X-ray diffraction pattern.
[9] A crystal of sulfate of Compound A, which shows diffraction peaks at diffraction angles 2θ of 10.3, 20.7, 20.9, 28.0, and 31.2° in a powder X-ray diffraction pattern (henceforth also referred to as "γ-form crystal").

The γ-form crystal can be distinguished from other crystal forms on the basis of the aforementioned diffraction peaks at the diffraction angles 2θ of 10.3, 20.7, 20.9, and 31.2°. These values are characteristic values of this crystal form.
[10] A pharmaceutical composition containing a crystal of sulfate of Compound A that shows diffraction peaks at diffraction angles 2θ of 10.3, 20.7, 20.9, and 31.2° in a powder X-ray diffraction pattern; or a crystal of sulfate of Compound A that shows diffraction peaks at diffraction angles 2θ of 10.3, 20.7, 20.9, 28.0, and 31.2° in a powder X-ray diffraction pattern.

[11] A method for preparing the crystal according to [2] or [3], which comprises the step of adding aqueous sulfuric acid to the crystal according to [5] or [6] to suspend the crystal, and stirring the suspension at 10 to 65° C., and wherein less than 4 moles of sulfuric acid is preferably used for 1 mole of Compound A or hydrate thereof.

[12] A method for preparing the crystal according to [5] or [6], which comprises the step of dissolving Compound A or hydrate thereof in aqueous sulfuric acid with heating, and gradually cooling the solution to allow deposition of the crystal.

[13] A method for preparing the crystal according to [8] or [9], which comprises the step of adding aqueous sulfuric acid to the crystal according to [5] or [6] to suspend the crystal, and stirring the suspension at 10 to 65° C., and wherein 4 moles or more of sulfuric acid is preferably used for 1 mole of Compound A or hydrate thereof.

Effect of the Invention

According to the present invention, there can be provided sulfate of Compound A having such superior properties as suppressed blue coloring, high purity, and/or low hygroscopic property, and showing high storage stability.

Furthermore, according to the present invention, there can be provided a crystal of sulfate of Compound A having such superior properties as suppressed blue coloring, high purity, and/or low hygroscopic property, and showing high storage stability.

MODES FOR CARRYING OUT THE INVENTION

Hereafter, the present invention will be explained in detail. In the present invention, a numerical range indicated with "to" means a range including the values mentioned before and after "to" as the maximum and minimum values of the range. In the present invention, when a composition contains a plurality of kinds of substances corresponding to one component of the composition, the amount of the component indicates the total amount of the plurality of kinds of substances contained in the composition, unless especially indicated.

The salt of the present invention include anhydride and hydrate thereof.

The crystal of the present invention includes a crystal containing anhydride or hydrate of the salt and a crystal having water of adhesion.

The term "diffraction angle 2θ of X°" used for a powder X-ray diffraction pattern of the crystal of the present invention means "diffraction angle 2θ of ((X−0.2) to (X+0.2))°", unless especially indicated.

The salt and a crystal thereof of the present invention show any one (preferably all) of the characteristics of (1) suppressed blue coloring, (2) high purity, (3) low hygroscopic property, and (4) superior storage stability, and are useful as an active pharmaceutical ingredient.

<Method for Preparing α-Form Crystal>

The α-form crystal can be prepared by dissolving Compound A or hydrate thereof in aqueous sulfuric acid with heating, and gradually cooling the solution to allow deposition of the crystal. Compound A or hydrate thereof can be prepared by, for example, the method described in Japanese Patent Unexamined Publication (Kokai) No. 58-24569, or the method described in Preparation Example 1 mentioned below.

The amount of sulfuric acid contained in the aqueous sulfuric acid may be 0.5 to 1.4 moles, preferably 1.0 to 1.2 moles, for 1 mole of Compound A or hydrate thereof.

The volume of the aqueous sulfuric acid to be used for dissolving Compound A or hydrate thereof is not particularly limited. For example, it is preferably 20- to 100-fold volume (v/w), more preferably 40- to 60-fold volume (v/w), of Compound A or hydrate thereof.

The temperature of heating for dissolving Compound A or hydrate thereof in aqueous sulfuric acid is not particularly limited. For example, it can be 40 to 60° C., preferably 50 to 60° C., more preferably 50 to 55° C.

The temperature for the deposition of the crystal is not particularly limited. For example, it can be 0 to 40° C., preferably 0 to 20° C., more preferably 0 to 10° C.

The time for the deposition of the crystal is not particularly limited. For example, it is preferably 0.5 to 24 hours, more preferably 0.5 to 6 hours.

<Method for Preparing β-Form Crystal>

The β-form crystal can be prepared by, for example, adding aqueous sulfuric acid to the α-form crystal to suspend the crystal, and stirring the suspension at 10 to 65° C. By allowing the deposition of the crystal, yield of the crystal can be improved.

The amount of sulfuric acid contained in the aqueous sulfuric acid is preferably 2 to 3 moles for 1 mole of Compound A in the form of the α-form crystal.

The volume of the aqueous sulfuric acid to be used is not particularly limited. For example, it is preferably 1- to 50-fold volume (v/w), more preferably 5- to 20-fold volume (v/w), of the α-form crystal.

The time for stirring the suspension is not particularly limited. For example, it is preferably 0.5 to 5 hours, more preferably 2 to 5 hours.

The time for allowing deposition of the crystal is not particularly limited. For example, it is preferably 12 to 24 hours.

<Method for Preparing γ-Form Crystal>

The γ-form crystal can be prepared by, for example, adding aqueous sulfuric acid to the α-form crystal to suspend the crystal, and stirring the suspension at 10 to 65° C. By allowing the deposition of the crystal, yield of the crystal can be improved.

The amount of sulfuric acid contained in the aqueous sulfuric acid is preferably 4 to 10 moles for 1 mole of Compound A in the form of the α-form crystal.

The volume of the aqueous sulfuric acid to be used is not particularly limited. For example, it is preferably 5- to 20-fold volume (v/w), more preferably 10- to 15-fold volume (v/w), of the α-form crystal.

The time for stirring the suspension is not particularly limited. For example, it is preferably 0.5 to 5 hours, more preferably 2 to 5 hours.

The time for allowing deposition of the crystal is not particularly limited. For example, it is preferably 12 to 24 hours.

At the time of preparing the α-form crystal, a seed crystal is preferably used. The crystalline form can be thereby controlled to be more uniform.

As the seed crystal, a crystal prepared in the previous preparation may be used, or a part of deposited crystals may be taken by filtration at the start of the preparation, and used as the seed crystal.

Although the temperature for collecting the α-, β-, or γ-form crystals prepared by deposition of crystal or stirring of the suspension by filtration is not particularly limited, it is preferably 0 to 25° C.

The deposition of crystal or stirring of the suspension can be performed in the air or in an inert gas atmosphere, and it is preferably performed in an inert gas atmosphere. Examples of the inert gas atmosphere include argon atmosphere, nitrogen atmosphere, and so forth.

<Pharmaceutical Composition>

The pharmaceutical composition of the present invention contains one or more kinds of crystals selected from the α-, β-, and γ-form crystals. The pharmaceutical composition of the present invention shows superior storage stability, because it contains the α-, β-, and/or γ-form crystal.

When the α-, β-, and/or γ-form crystal is used as a pharmaceutical composition, pharmaceutical auxiliaries usually used for production of pharmaceutical preparations such as excipients, carriers, and diluents may be appropriately mixed. The composition can be orally or parenterally administered in a conventional manner in the form of tablet, capsule, powder, syrup, granule, pill, suspension, emulsion, solution, powdery preparation, suppository, eye drop, nose drop, ear drop, patch, ointment, injection, or the like. The administration method, dose and frequency can be appropriately chosen according to patient's age, weight, and symptoms. To an adult, 0.01 to 2000 mg/kg per day of the salt can be usually administered orally or parenterally (by, for example, injection, drip infusion, administration to rectal part, or the like) once a day, or several times a day with dividing the foregoing dose.

Hereafter, the present invention will be specifically explained with reference to examples, preparation examples, and pharmaceutical preparation example. However, the present invention is not limited by these. Unless especially indicated, % means mass %.

The meaning of the abbreviation used in the following descriptions is as follows.

HPLC: High performance liquid chromatography

Powder X-ray diffraction was measured by using UltimaIV (Rigaku) under the following conditions.

(Measurement Conditions)

Counter cathode: Cu

Tube voltage: 40 kV

Tube current: 40 mA

Scanning axis: 2θ

The infrared absorption spectra were measured by using Spectrum One (PerkinElmer) according to the descriptions of the Japanese Pharmacopoeia, General Test Procedures, Attenuated Total Reflection Fourier Transform Infrared Spectrometry Method (ATR method).

The moisture content was measured with a Karl-Fischer moisture meter.

The purities are represented in terms of HPLC area %. The HPLC measurement was performed by using Prominence (Shimadzu) under the following conditions.

(Measurement Conditions)

Measurement wavelength: 210 nm

Column: Hydrosphere C18 (internal diameter 6.0 mm×length 250 mm, particle diameter 5 μm)

Column temperature, 40° C.

Flow rate: 0.8 mL/minute

Solution A for mobile phase: water (950 mL) and 0.4 mol/L phosphate/triethylamine buffer (pH 3, 50 mL)

Solution B for mobile phase: water (50 mL), acetonitrile (900 mL), and 0.4 mol/L phosphate/triethylamine buffer (pH 3, 50 mL)

As the mobile phase, mixtures of the solutions A and B for mobile phase were used as the following linear gradient.

TABLE 1

| Time (minute) | Volume ratio of solution A for mobile phase (%) | Volume ratio of solution B for mobile phase (%) |
| --- | --- | --- |
| 0 | 98 | 2 |
| 10 | 98 | 2 |
| 20 | 90 | 10 |
| 30 | 90 | 10 |
| 45 | 0 | 100 |
| 55 | 0 | 100 |

PREPARATION EXAMPLE 1

(1) Under a nitrogen atmosphere, 2-aminomalonamide (30 g, Tateyama Kasei) and oxalic acid (115 mg) were added to 2-propanol (600 mL), the mixture was heated to 82° C., and then triethyl orthoformate (106 mL, purity 99.5%, Nippoh Chemicals) was added dropwise to the mixture over 10 minutes. Then, the reaction mixture was stirred at 84° C. for 7 hours and 30 minutes. The reaction mixture was cooled to 57° C., and then water (30 mL) and concentrated hydrochloric acid (24 mL) were successively added to the reaction mixture. The reaction mixture was cooled to 5° C., and the crystals were collected by filtration, and washed with acetone (120 mL) to obtain 5-hydroxy-1H-imidazole-4-carboxamide hydrochloride dihydrate as pale yellow crystals (49 g).

(2) Under a nitrogen atmosphere, 5-hydroxy-1H-imidazole-4-carboxamide hydrochloride dihydrate (20.0 g) was added to 0.45 mol/L hydrochloric acid (240 mL), and dissolved by heating the mixture to 50° C. To this solution, a solution of sodium formate (14.3 g) in water (40 mL) was added dropwise over 33 minutes. The reaction mixture was cooled to 5° C., and the crystals were collected by filtration, washed with a mixture of acetone (20 mL) and water (40 mL), and then washed with acetone (60 mL) to obtain 5-hydroxy-1H-imidazole-4-carboxamide 3/4 hydrate as pale yellow crystals (12.8 g).

EXAMPLE 1

To 5-hydroxy-1H-imidazole-4-carboxamide 3/4 hydrate (1.5 g), water (30 mL) and concentrated sulfuric acid (625 μL) were added, the mixture was heated to 50 to 55° C., then water (45 mL) was further added to dissolve the compound, and the mixture was stirred at the same temperature for 30 minutes. The reaction mixture was gradually cooled to room temperature. After the deposition of crystals was confirmed, the mixture was cooled on ice, and the crystals were collected by filtration. The crystals were washed with water and air-dried to obtain α-form crystals (1.8 g).

The α-form crystals showed characteristic peaks at diffraction angles 2θ of 10.0, 13.7, 14.6, 17.0, 18.0, 20.1, 24.4, 25.2, and 28.1° in the powder X-ray diffraction pattern.

The α-form crystals also showed characteristic peaks at 1563, 1504, 1456, 1390, 1050, and 863 cm$^{-1}$ in the infrared absorption spectrum.

Figure 3:
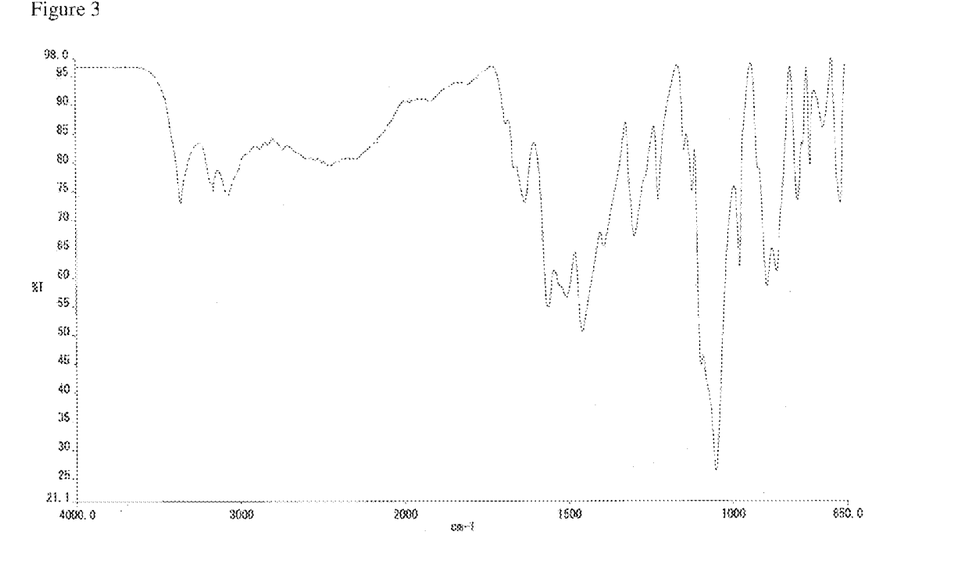
FIG. 3 shows an example of infrared absorption spectrum (ATR method) of the α-form crystal.
Figure 4:
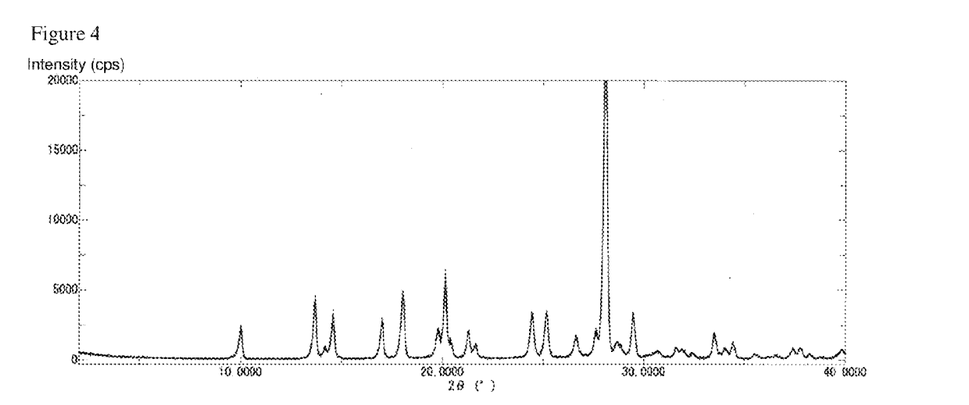
FIG. 4 shows an example of powder X-ray diffraction pattern of the α-form crystal.

The infrared absorption spectrum (ATR method) of the α-form crystals is shown in FIG. 3, and the powder X-ray diffraction pattern of the same is shown in FIG. 4 and Table 2.

The moisture content of the α-form crystals was 9.1%.

TABLE 2

| 2θ (°) | d Value (Å) | Relative intensity (%) |
|---|---|---|
| 10.0 | 8.8 | 9 |
| 13.7 | 6.5 | 17 |
| 14.6 | 6.1 | 13 |
| 17.0 | 5.2 | 11 |
| 18.0 | 4.9 | 19 |
| 20.1 | 4.4 | 24 |
| 24.4 | 3.6 | 13 |
| 25.2 | 3.5 | 14 |
| 28.1 | 3.2 | 100 |

EXAMPLE 2

To α-form crystals (4.0 g) prepared according to the method described in Example 1, 1 mol/L aqueous sulfuric acid (40 mL) was added, and the mixture was stirred at room temperature for 2 hours and 45 minutes under a nitrogen atmosphere. To the reaction mixture, 1 mol/L aqueous sulfuric acid (20 mL) was added, then the mixture was left overnight, and further stirred for 1 hour and 30 minutes, and the crystals were collected by filtration. The crystals were washed with 1 mol/L aqueous sulfuric acid and acetone, and air-dried to obtain β-form crystals (3.7 g).

The β-form crystals showed characteristic peaks at diffraction angles 2θ of 5.0, 10.1, 13.6, 14.3, 14.7, 20.3, 27.4, 28.0, 28.8, and 29.6° in the powder X-ray diffraction pattern.

The β-form crystals also showed characteristic peaks at 1560, 1508, 1459, and 1059 cm$^{-1}$ in the infrared absorption spectrum.

Figure 1:
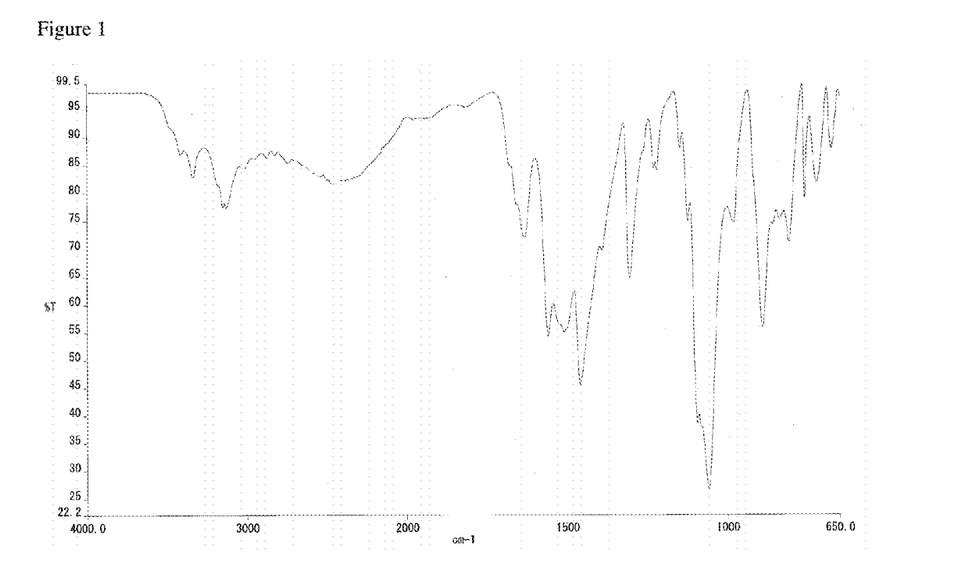
FIG. 1 shows an example of infrared absorption spectrum (ATR method) of the β-form crystal.
Figure 2:
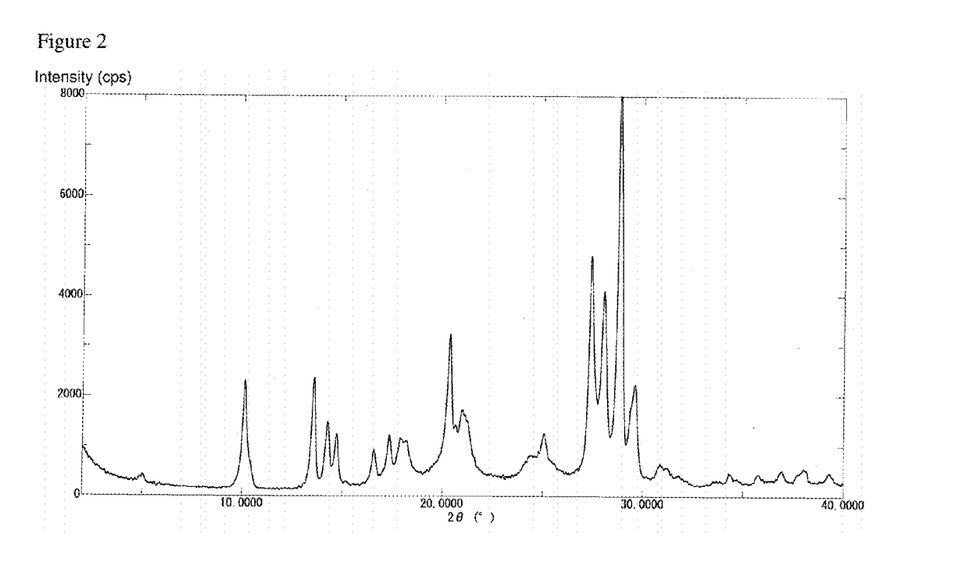
FIG. 2 shows an example of powder X-ray diffraction pattern of the β-form crystal.

The infrared absorption spectrum (ATR method) of the β-form crystals is shown in FIG. 1, and the powder X-ray diffraction pattern of the same is shown in FIG. 2 and Table 3.

The moisture content of the β-form crystals was 8.1%.

TABLE 3

| 2θ (°) | d Value (Å) | Relative intensity (%) |
|---|---|---|
| 5.0 | 17.6 | 3 |
| 10.1 | 8.7 | 27 |
| 13.6 | 6.5 | 27 |
| 14.3 | 6.2 | 16 |
| 14.7 | 6.0 | 13 |
| 20.3 | 4.4 | 32 |
| 27.4 | 3.3 | 55 |
| 28.0 | 3.2 | 39 |
| 28.8 | 3.1 | 100 |
| 29.6 | 3.0 | 21 |

EXAMPLE 3

To α-form crystals (0.5 g) prepared according to the method described in Example 1, 2 mol/L aqueous sulfuric acid (5 mL) was added, and the mixture was stirred at room temperature for 3 hours and 20 minutes. To the reaction mixture, concentrated sulfuric acid (1 mL) was further added, and then the mixture was stirred for 4 hours and 40 minutes. The mixture was left overnight, and then the crystals were collected by filtration. The crystals were washed with acetone, and air-dried to obtain γ-form crystals (0.5 g).

The γ-form crystals showed characteristic peaks at diffraction angles 2θ of 10.3, 20.7, 20.9, 28.0, and 31.2° in the powder X-ray diffraction pattern.

The γ-form crystals also showed characteristic peaks at 1560, 1503, 1459, 1304, 1061, and 892 cm$^{-1}$ in the infrared absorption spectrum.

Figure 5:
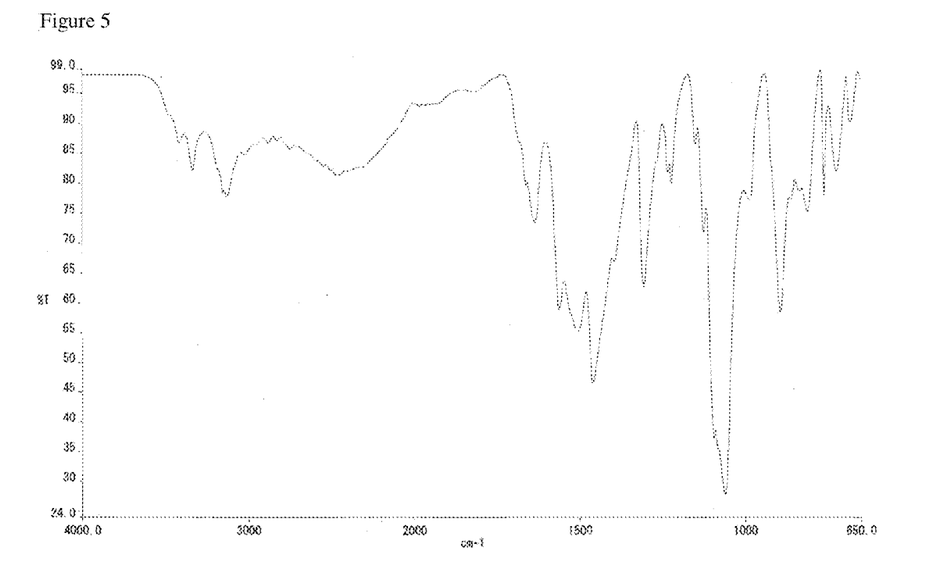
FIG. 5 shows an example of infrared absorption spectrum (ATR method) of the γ-form crystal.
Figure 6:
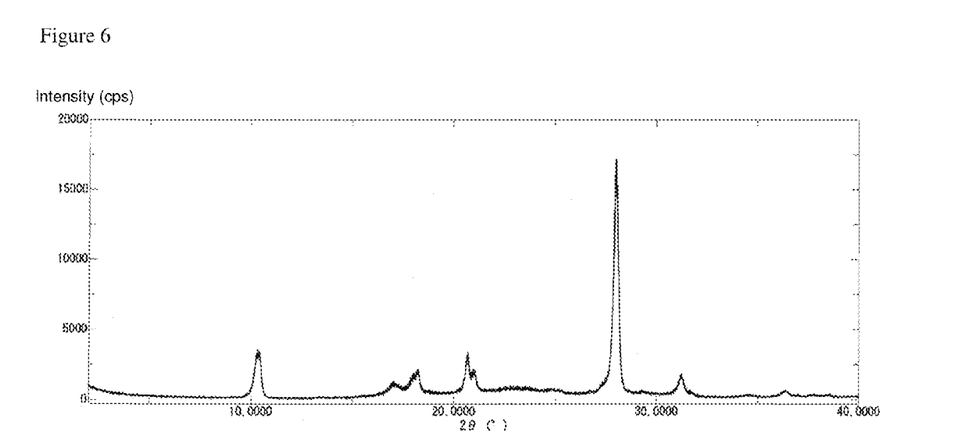
FIG. 6 shows an example of powder X-ray diffraction pattern of the γ-form crystal.

The infrared absorption spectrum (ATR method) of the γ-form crystals is shown in FIG. 5, and the powder X-ray diffraction pattern of the same is shown in FIG. 6 and Table 4.

The moisture content of the γ-form crystals was 4.1%.

TABLE 4

| 2θ (°) | d Value (Å) | Relative intensity (%) |
|---|---|---|
| 10.3 | 8.5 | 19 |
| 20.7 | 4.3 | 19 |
| 20.9 | 4.2 | 12 |
| 28.0 | 3.2 | 100 |
| 31.2 | 2.9 | 11 |

COMPARATIVE EXAMPLE 1

5-Hydroxy-1H-imidazole-4-carboxamide was obtained as pale yellow powder according to the method described in International Publication WO2009/035168, Example 6.

As a result of high performance liquid chromatography analysis, the obtained 5-hydroxy-1H-imidazole-4-carboxamide contained about 0.15% of benzoic acid.

Figure 7:
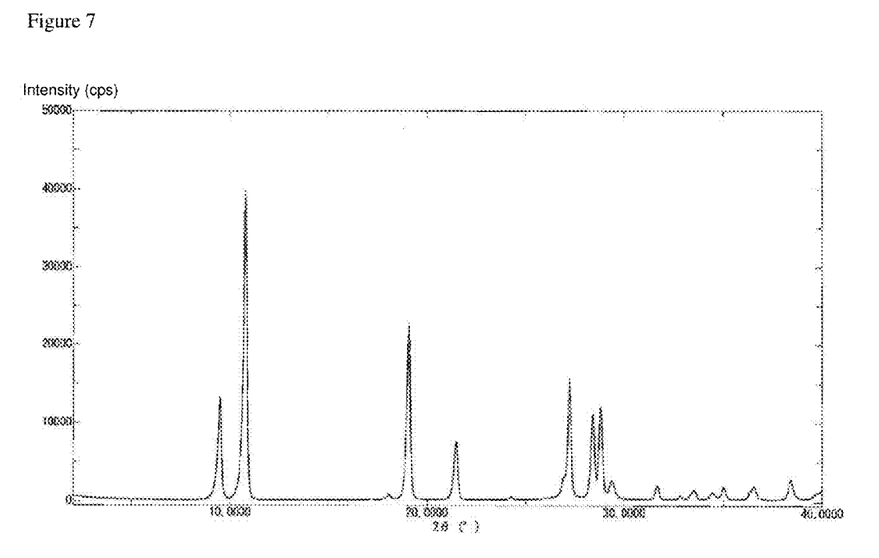
FIG. 7 shows an example of powder X-ray diffraction pattern of the crystal of Compound A obtained in Comparative Example 1.

The powder X-ray diffraction pattern thereof is shown in FIG. 7 and Table 5.

TABLE 5

| 2θ (°) | d Value (Å) | Relative intensity (%) |
|---|---|---|
| 9.5 | 9.3 | 33 |
| 10.8 | 8.2 | 100 |
| 19.1 | 4.7 | 60 |
| 21.4 | 4.1 | 20 |
| 27.2 | 3.3 | 43 |

TABLE 5-continued

| 2θ (°) | d Value (Å) | Relative intensity (%) |
|---|---|---|
| 28.4 | 3.1 | 30 |
| 28.8 | 3.1 | 32 |

COMPARATIVE EXAMPLE 2

Methanesulfonate of 5-hydroxy-1H-imidazole-4-carboxamide was prepared as described below with reference to the method described in International Publication WO2009/035168, Example 3.

To 5-hydroxy-1H-imidazole-4-carboxamide 3/4 hydrate (1.4 g), water (30 mL) and methanesulfonic acid (1.0 g) were added, the mixture was heated at 50° C. to dissolve the compounds, and then the solution was stirred at the same temperature for 30 minutes. After the reaction mixture was cooled to room temperature, toluene was added, water was removed by azeotropy under reduced pressure, and the precipitated solid was collected by filtration. The solid was washed with ethyl acetate and air-dried to obtain methanesulfonate of 5-hydroxy-1H-imidazole-4-carboxamide (1.7 g).

The moisture content of the methanesulfonate of 5-hydroxy-1H-imidazole-4-carboxamide was 7.8%.

TEST EXAMPLE 1

Storage Stability Test (1) Under Conditions of 60° C. and Relative Humidity of 75%

As test substances, the crystals obtained in Examples 1 and 2 and Comparative Example 1 were chosen.

Each test substance (about 0.3 g) was put into a glass bottle, and stored under the conditions of 60° C. and relative humidity of 75% for 2 weeks.

Figure 8:
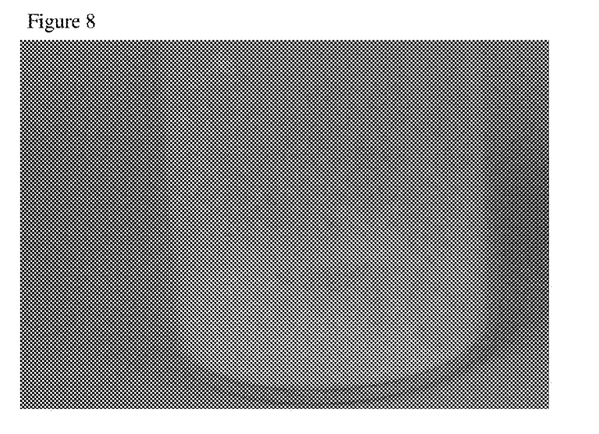
FIG. 8 is a photograph showing the α-form crystals of sulfate of Compound A after storage for two weeks under the conditions of 60° C. and relative humidity of 75%.
Figure 9:
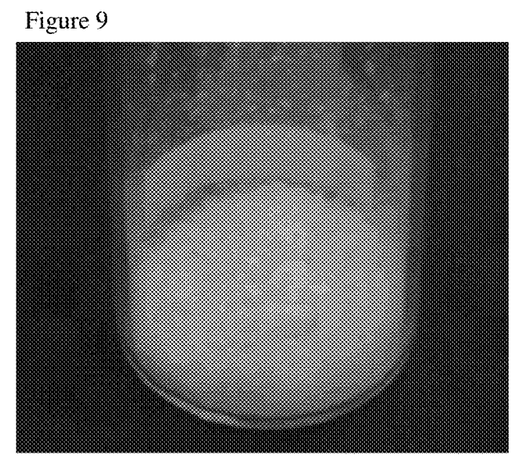
FIG. 9 is a photograph showing the β-form crystals of sulfate of Compound A after storage for two weeks under the conditions of 60° C. and relative humidity of 75%.
Figure 10:
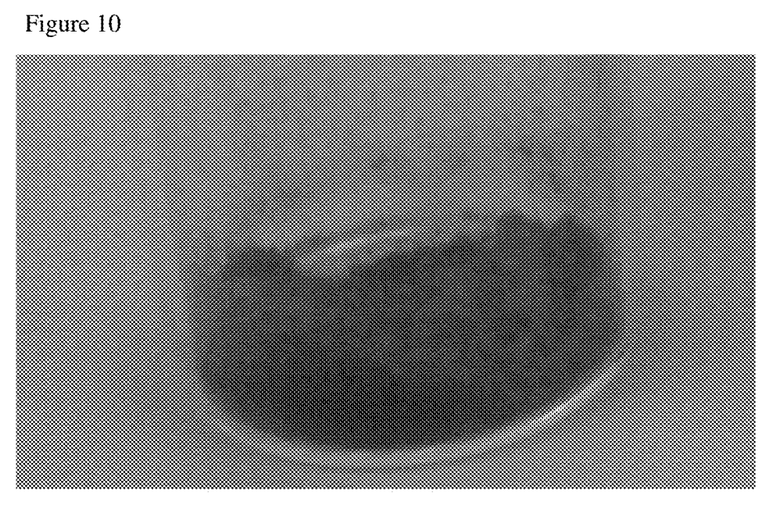
FIG. 10 is a photograph showing crystals of Compound A after storage for two weeks under the conditions of 60° C. and relative humidity of 75%.

The crystals of Examples 1 and 2 after the test are shown in FIGS. 8 and 9, respectively. The crystals of Comparative Example 1 after the test are shown in FIG. 10.

The crystals obtained in Examples 1 and 2 showed coloring in an obviously lower degree compared with the crystals obtained in Comparative Example 1, and thus showed superior storage stability.

TEST EXAMPLE 2

Storage Stability Test (2) Under Conditions of 60° C. and Relative Humidity of 75%

As a test substance, the crystals obtained in Example 1 were chosen.

The test substance (about 0.3 g) was put into a glass bottle, and stored under the conditions of 60° C. and relative humidity of 75% for 2 weeks. After completion of the test, purity of the substance was measured by HPLC. As a result, the purity of the test substance was found to be 99.97%.

The crystals obtained in Example 1 showed high purity even after the storage for 2 weeks, and thus showed superior storage stability.

The crystals obtained Example 2 also showed high purity even after the storage for 2 weeks in an evaluation performed in the same manner as that of Test Example 2, and thus showed superior storage stability.

TEST EXAMPLE 3

Storage Stability Test (3) Under Conditions of 60° C. and Relative Humidity of 75%

As test substances, the crystals obtained in Example 2 and Comparative Example 2 were chosen.

Each test substance (about 0.3 g) was put into a glass bottle, and stored under the conditions of 60° C. and relative humidity of 75% for 2 weeks, and then mass was measured. Mass change ratio of each test substance was calculated according to the following equation.

Mass change ratio(%)=$\{(A_1-A_0)/A_0\} \times 100$ $A_0$: Mass (g) of test substance before test
$A_1$: Mass (g) of test substance after test Change of color appearance of the test substances was also visually evaluated.

The results are shown in Table 6.

TABLE 6

| | Mass change ratio (%) | Change of color appearance |
|---|---|---|
| Example 2 | −0.1 | No change (white) |
| Comparative Example 2 | +16.2 | Observed (changed from pale yellow to yellow) |

The crystals obtained in Example 2 showed lower hygroscopic property compared with the crystals obtained in Comparative Example 2, and showed no change of color appearance.

Further, when these crystals were stored for 2 weeks under the conditions of 25° C. and relative humidity of 97%, the crystals obtained in Example 2 did not show appearance change, and thus were stable, whereas the crystals obtained in Comparative Example 2 deliquesced, and thus were unstable.

PHARMACEUTICAL PREPARATION EXAMPLE 1

A pharmaceutical composition containing the salt of the present invention or crystals thereof can be prepared in, for example, the following composition.
Tablet

| | |
|---|---|
| (1) Crystals obtained in Example 2 | 221.3 mg |
| (2) Lactose hydrate | 13.9 mg |
| (3) Carmellose calcium | 22.4 mg |
| (4) Hydroxypropyl cellulose | 8.4 mg |
| (5) Light anhydrous silicic acid | 8.4 mg |
| (6) Magnesium stearate | 5.6 mg |
| Weight of one tablet | 280 mg |

The ingredients of (1), (2), and (3) are mixed, the ingredient of (4) is sprayed on the powdery mixture, the mixture is granulated, the ingredients (5) and (6) are mixed with the granulated mixture, and the mixture is made into tablets.

INDUSTRIAL APPLICABILITY

The salt and a crystal thereof of the present invention show such characteristics as (1) suppressed blue coloring, (2) high purity, (3) low hygroscopic property, and (4) superior storage stability, and are useful as a active pharmaceutical ingredient of drugs.

The invention claimed is:

1. Sulfate of 5-hydroxy-1H-imidazole-4-carboxamide.

2. A crystal of sulfate of 5-hydroxy-1H-imidazole-4-carboxamide.

3. A pharmaceutical composition containing a crystal of sulfate of 5-hydroxy-1H-imidazole-4-carboxamide.

4. The crystal according to claim 2, which shows diffraction peaks at diffraction angles 2θ of 5.0, 20.3, and 29.6° in a powder X-ray diffraction pattern.

5. The crystal according to claim 2, which shows diffraction peaks at diffraction angles 2θ of 5.0, 10.1, 13.6, 14.3, 14.7, 20.3, 27.4, 28.0, 28.8, and 29.6° in a powder X-ray diffraction pattern.

6. The pharmaceutical composition according to claim 3:
wherein the crystal shows diffraction peaks at diffraction angles 2θ of 5.0, 20.3, and 29.6° in a powder X-ray diffraction pattern; or
the crystal shows diffraction peaks at diffraction angles 2θ of 5.0, 10.1, 13.6, 14.3, 14.7, 20.3, 27.4, 28.0, 28.8, and 29.6° in a powder X-ray diffraction pattern.

7. The crystal according to claim 2, which shows diffraction peaks at diffraction angles 2θ of 13.7, 17.0, 18.0, and 20.1° in a powder X-ray diffraction pattern.

8. The crystal according to claim 2, which shows diffraction peaks at diffraction angles 2θ of 10.0, 13.7, 14.6, 17.0, 18.0, 20.1, 24.4, 25.2, and 28.1° in a powder X-ray diffraction pattern.

9. The pharmaceutical composition according to claim 3:
wherein the crystal shows diffraction peaks at diffraction angles 2θ of 13.7, 17.0, 18.0, and 20.1° in a powder X-ray diffraction pattern; or
the crystal shows diffraction peaks at diffraction angles 2θ of 10.0, 13.7, 14.6, 17.0, 18.0, 20.1, 24.4, 25.2, and 28.1°.

10. The crystal according to claim 2, which shows diffraction peaks at diffraction angles 2θ of 10.3, 20.7, 20.9, and 31.2° in a powder X-ray diffraction pattern.

11. The crystal according to claim 2, which shows diffraction peaks at diffraction angles 2θ of 10.3, 20.7, 20.9, 28.0, and 31.2° in a powder X-ray diffraction pattern.

12. The pharmaceutical composition according to claim 3:
wherein the crystal shows diffraction peaks at diffraction angles 2θ of 10.3, 20.7, 20.9, and 31.2° in a powder X-ray diffraction pattern; or
the crystal shows diffraction peaks at diffraction angles 2θ of 10.3, 20.7, 20.9, 28.0, and 31.2° in a powder X-ray diffraction pattern.

* * * * *